US010086036B2

(12) United States Patent
Rotunda

(10) Patent No.: US 10,086,036 B2
(45) Date of Patent: Oct. 2, 2018

(54) BLEOMYCIN-BASED COMPOSITIONS AND USE THEREOF FOR TREATING LOOSE SKIN AND FATTY TISSUE

(71) Applicant: Adam M. Rotunda, Irvine, CA (US)

(72) Inventor: Adam M. Rotunda, Irvine, CA (US)

( * ) Notice: Subject to any disclaimer, the term of this patent is extended or adjusted under 35 U.S.C. 154(b) by 0 days.

(21) Appl. No.: 15/241,458

(22) Filed: Aug. 19, 2016

(65) Prior Publication Data

US 2018/0050080 A1    Feb. 22, 2018

(51) Int. Cl.
*A61K 38/14*    (2006.01)
*A61K 9/00*    (2006.01)
*A61K 9/70*    (2006.01)

(52) U.S. Cl.
CPC ............ *A61K 38/14* (2013.01); *A61K 9/0014* (2013.01); *A61K 9/0019* (2013.01); *A61K 9/7023* (2013.01)

(58) Field of Classification Search
None
See application file for complete search history.

(56) References Cited

U.S. PATENT DOCUMENTS

| | | | |
|---|---|---|---|
| 3,664,006 | A | 5/1972 | Valle |
| 9,232,016 | B2 | 1/2016 | Caskey et al. |
| 2006/0293725 | A1 | 12/2006 | Rubinsky et al. |
| 2009/0053290 | A1 | 2/2009 | Sand et al. |
| 2013/0012590 | A1 | 1/2013 | Zadini et al. |
| 2014/0004206 | A1 | 1/2014 | Kolodney et al. |
| 2014/0141100 | A1 | 5/2014 | Marino et al. |

FOREIGN PATENT DOCUMENTS

WO    2009111648    9/2009

OTHER PUBLICATIONS

American Academy of Dermatology ('The layers of your skin' retrieved from https://www.aad.org/public/kids/skin/the-layers-of-your-skin on Oct. 11, 2017, 3 pages) (Year: 2017).*
Definition of displace (retrieved from http://www.dictionary.com/browse/displace on Oct. 11, 2017, 5 pages) (Year: 2017).*
NCBI ('Skin and connective tissue' retrieved from https://www.ncbi.nlm.nih.gov/books/NBK22247/ on Oct. 11, 2017, 2 pages) (Year: 2017).*
Slyper AH ('Childhood obesity, adipose tissue distribution, and the pediatric practitioner' Pediatrics v102(1) Jul. 1998 pp. 1-9) (Year: 1998).*
WebMD ('How to deal with extra, loose skin after losing a lot of weight' retrieved from https://www.webmd.com/diet/obesity/features/you-lost-weight-what-about-extra-skin on Oct. 11, 2017, 19 pages) (Year: 2017).*
Livehealthy ('Can loose skin be tightened with muscle growth?' retrieved from http://livehealthy.chron.com/can-loose-skin-tightened-muscle-growth-4080.html on Oct. 11, 2017, 3 pages) (Year: 2017).*

Horbach MD, Sophie, E.R., et al.; Intralesional bleomycin injections for vascular malformations: A systematic review and meta-analysis; American Society of Plastic Surgeons at www.PRSJournal.com; 2015; pp. 244-256.
Door, RT; Bleomycin pharmacology; mechanism of action and resistance, and clinical pharmacokinetics/Abstract; Semin Oncol.; Apr. 1992; 19(2, Suppl 5): 3-8.
Parker, James C.;Acute lung injury and pulmonary vascular permeability: Use of transgenic models; Published online Comprehensive Physiology; vol. 1, Apr. 2011; pp. 835-882.
Kirby, MD, Joslyn SL. et al.; Intralesional chemotherapy for nonmelanoma skin cancer: A practical review; Published on line by the American Academy of Dermatology, Inc.;, Jun. 1, 2010; p. 689-702.
Saitta, BA, Peter, et al.; Bleomycin in dermatology; A review of intralesional applications; Published by the American Society for Dermatologic Surgery, Inc.;, 2008; 34:1299-1313.
Wang, MD, Hui, et al.; Treatment of Xanthelasma palpebrarum with intralesional pingyangmycin; American Society for Dermatologic Surgery, Inc.;, 2016; 42: 368-376.
Batteaux, Frederic, et al.; New insights on chemically induced animal models of systemic sclerosis; Current Opinion in Rheumatology 2011; 23:511-518.
Bauer, M.D., Kenneth A., et al.; Pulmonary complications associated with combination chemotherapy programs containing bleomycin; The American Journal of Medicine; Apr. 1983; vol. 74; pp. 557-563.
Biswas, Ahitagni, et al.; Bleomycin induced flagellate erythema: Revisiting a unique complication; Journal of Cancer Research and Therapeutics; 2013; vol. 9; Issue 3; pp. 500-503.
Blum, MD, Ronald H., et al.; A clinical review of bleomycin—a new antineoplastic agent; Cancer; Published Oct. 2, 1972; pp. 903-914.
Churchill, Paige, et al.; Sclerotherapy for lymphatic malformations in children: a scoping review; Journal of Pediatric Surgery; (2011) 46, 912-922.
Della Latta, Veronica, et al.; Bleomycin in the setting of lung fibrosis induction: From biological mechanisms to counteractions; Pharmacological Research 97 (2015) 122-130.
Eivazi, Behfar, et al.; Extracranial vascular malformations (hemangiomas and vascular malformations) in children and adolescents—diagnosis, clinic, and therapy; GMS Current Topics in Otorhinolaryngology, Head and Neck Surgery; 2014; vol. 13; pp. 1-19.
Grynszpan, Rachel, et al.; Case Report: Bleomycin-induced flagellate dermatitis;BMJ Case Rep 2013; doi:10.1136/bcr-2013-009764; 3 pages.
Haugnes, Hege S., et al.; Pulmonary and cardiovascular toxicity in long-term testicular cancer survivors; Urologic Oncology; Seminars and Original Investigations 33 (2015) 399-406.

(Continued)

*Primary Examiner* — Karlheinz R. Skowronek
*Assistant Examiner* — Ronald T Niebauer
(74) *Attorney, Agent, or Firm* — Stetina Brunda Garred & Brucker

(57) ABSTRACT

A composition for displacing loose skin and removing subcutaneous deposits of fatty tissue. The composition includes effective amounts of one or more bleomycin-type drugs that are operative to cause apoptosis in localized fat cells, thus causing permanent eradication of such cells. Loose skin is likewise displaced with dense fibrous tissue produced via selective scarring induced by the active bleomycin-type drugs. The compositions are formulated as creams, lotions, gels, waxes, foams, sprays and the like for selectively applied, local topical application, and may also be administered as a conventional transdermal patch. The compositions may alternatively be formulated to be injected into the skin.

15 Claims, No Drawings

(56) References Cited

OTHER PUBLICATIONS

Hiruta, Yuka, et al.; Novel ultra-deformable vesicles entrapped with bleomycin and enhanced to penetrate rat skin; Journal of Controlled Release; 113 (2006); 146-154.

Horbach, Sophie E.R, et al.; Sclerotherapy for low-flow vascular malformations of the head and neck: A systematic review of sclerosing agents; Journal of Plastic, Reconstructive &, Aesthetic Surgery (2016) 69; 295-304.

Jun-Bo Tu et al.; Pingyangmycin stimulates apoptosis in human hemangioma-derived endothelial cells through activation of the p53 pathway; Spandidos Publications; Apr. 24, 2014; 9 pages; https://www.ncbi.nlm.nih.gov/pmc/articles/PMC3664006.

Juniantito, V. et al.; Immunophenotypical Characterization of Macrophages in Rat Belomycin-Induced Scleroderma; Animal Models; Veterinary Pathology; 2012; 50(1): 76-85.

Kandeel, Samah, et al.; The possible protective effect of simvastatin and pioglitazone separately and in combination on bleomycin-induced changes in mice thin skin; Tissue and Cell 47 (2015) 159-170.

Ledon, BS, Jennifer A., et al., ; Intralesional treatment for keloids and hypertrophic scars: A review; Dermatologic Surgery;, Published online Nov. 13, 2013.

Martins, Vanessa, et al.; Cell injury, repair, aging, and apoptosis: FIZZ1-Induced myofibroblast transdifferentiation from adipocytes and its potential role in dermal fibrosis and lipoatrophy; American Journal of Pathology, vol. 185, No. 10, Oct. 2015, pp. 2768-2776.

Muir, T., et al.; Intralesional bleomycin injection (IBI) treatment for haemangiomas and congenital vascular malformationS; Published online Pediatr. Surg. Int. (2004) 19: 766-773.

MacIntosh, Peter W., et al.; Complications of Intralesional bleomycin in the treatment of orbital lymphatic malformations; Seminars in, Opthamology; 2014; 29(5-6); 450-455.

McLeod, MD, Beverly F., et al.; Fatal bleomycin toxicity from a low cumulative dose in a patient with renal insufficiency; Cancer; 60: 2617-2620; 1987.

Samuels, MD, Melvin L., et al.; Large-dose bleomycin therapy and pulmonary toxicity—A possible role of prior radiotherapy; JAMA, Mar. 15, 1976; vol. 235, No. 11; pp. 1117-1120.

Serratrice et al.; New fat-derived products for treating skin-induced lesions of scleroderma in nude mice; Stem Cell Research &, Therapy 2014; 5:138; 10 pages.

www.urmc.rochester.edu/childrens-hospital/craniofacial/vascul . . . ; What is a Vascular Birthmark:; printed May 12, 2016.

Shippee, Brittney M. et al.; The role of screening and monitoring for bleomycin pulmonary toxicity; Journal of Oncology Pharmacy Practice; 2016, vol. 22(2), 308-312.

Sleijfer, MD, PhD, Stefan; Bleomycin-induced pneumonitis;, Chest; Aug. 2001; 120:617-624.

http://www.dermnetnz.org/treatments/bleomycin.html; Bleomycin: Skin side effects and intralesional use for skin conditions; BioMed Central Ltd.; 2016.

Tandon, Vishal R. et al.; Bleomycin containing chemotherapeutic regimen induced acquired partial lipodystrophy; Indian Journal of Dermatology; 2016; vol. 61; Issue 1; p. 122.

Kwok, CS, et al.; topical treatments for cutaneous warts (Review); Cochrane Library Cochrane Database of Systematic Reviews; 2012, Issue 9, 178 pages.

Taveira, Stephania Fleury et al.; Topical Administration of Anticancer Drugs for Skin Cancer Treatment; 2011; InTech; http://www.intechopen.com/books/skin-cancers-risk-factors-prevention-and-therapy/topical-administration-of-anticancer-drugs-for-skin-cancer-treatment.

Yamamoto, Toshiyuki et al.; Animal Model of Sclerotic Skin, I: Local Injections of Bleomycin Induce Sclerotic Skin Mimicking Scleroderma; The Society for Investigative Dermatology, Inc.; 1999; p. 456-462.

Van Der Vleuten, Carine J.M., et al.; Effectiveness of sclerotherapy, surgery, and laser therapy in patients with venous malformations; A systematic review; Cardiovasc, Intervent, Radiol. (2014) 37:977-989.

Vennepureddy, et al.; Bleomycin-induced flagellate erythema in a patient with Hodgkins lymphoma—A case report and review of literature; Journal of Oncology Pharmacy Practice; 2016; vol. 22(3); 556-560.

Wilson, MS FRCP, FACP, MRCP, Kenneth S., et al.; Low-dose bleomycin lung; Medical and Pediatric Oncology; 10:283-288 (1982).

Zheng, Jia Wei et al.; Guidelines for the treatment of head and neck venous malformations; International Journal of Clinical and Experimental Medicine; 2013; 6(5): 377-389 http://www.ncbi.nlm.nih.gov/pmc/articles/PMC3664006.

Zheng, J. et al; Intracystic bleomycin for cystic craniopharynglomas in children (Review); Cochrane Library; Cochrane Database of Systematic Reviews; 2014; Issue 9, 20 pages.

Lau, Kent G., et al.; Ultra-deformable liposomes containing bleomycin; In vitro stability and toxicity on human cutaneous keratinocyte cell lines; International Journal of Pharmaceutics; 300 (2005) 4-12.

Chen, Jingyang, et al.; Bleomycins: Towards better therapeutics; Feb. 2005; vol. 5; pp. 102-112.

Froudarakis, Marios, et al.; Revisiting bleomycin from pathophysiology to safe clinical use; Critical Reviews in Oncology Hematology; 87 (2013) 90-100.

Epstein, Joel B, et al.; Topical bleomycin for the treatment of dysplastic oral leukoplakia; Cancer; Aug. 15, 1998; vol. 83; No. 4; 6 pages.

PCT International Search Report and Written Opinion; PCT/US17/46614; dated Oct. 18, 2017; 8 pages.

Corrected: PCT International Search Report and Written Opinion; PCT/US17/46614; dated Dec. 18, 2017; 9 pages.

Ishikawa, H. et al; "Induction of Autoimmunity in a Bleomycin-induced Murine Model of Experimental Systemic Sclerosis: An Important Role for DC4+ T Cells"; Jan. 22, 2009, Journal of Investigative Dermatology; vol. 129; pp. 1688-1695; entire document.

Akashi, K et at; "Knockout of endothelin type B receptor signaling attenuates bleomycin-induced skin sclerosis in mice"; May 21, 2016, Arthritis Research & Therapy; vol. 18, article 113, pp. 1-9; entire document.

* cited by examiner

BLEOMYCIN-BASED COMPOSITIONS AND USE THEREOF FOR TREATING LOOSE SKIN AND FATTY TISSUE

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention is directed to compositions and methods for reducing subcutaneous fat deposits and tightening loose skin.

As the skin naturally ages, skin loosens and sags. These conditions can become exacerbated further by habitual facial expressions or sleeping patterns, as well as poor hydration. Exposure to ultraviolet radiation and tobacco smoke can also accelerate the skin's aging process. Despite such factors and the inevitability of the aging process, however, having a youthful appearance in society is highly prized, and many people have a strong desire to maintain and rejuvenate their appearance as much as they possibly can. In this regard, wrinkles, loose sagging skin, poor skin tone or texture, and other skin abnormalities are often considered to be visually unappealing and have proved to be difficult and vexing problems to treat, although the demand for effective treatments has been and remains quite high.

Among the options to treat such conditions include conventional surgical therapies (e.g., a face lift, brow lift, or liposuction), which can be effective to treat loose, fatty skin but are often invasive, inconvenient, and expensive, and resultant scarring can limit their applicability. Moreover, for small fat deposits, such those occurring with aging in some areas of the face, surgical techniques such as liposuction are often too aggressive and associated with well-known complications or risks, including temporary bruising, swelling, numbness or hypersensitivity, soreness and burning sensation, risk of infection, and pigmentation changes.

Alternative methods that are minimally invasive are also available; however, such methods are generally less effective than surgical methods. For example, methods using energy sources (e.g., laser, non-coherent light, radiofrequency, or ultrasound) or physical trauma (i.e., microneedling, also known as collagen induction therapy) can be effective at improving the architecture and the texture of the skin but are much less effective at tightening the skin or reducing skin laxity. As a further alternative, neurotoxins, such as botulinum toxin, can reduce the formation of dynamic wrinkles by paralysis of the injected muscles, but such toxins have minimal or no effect on skin tightness or laxity. Finally, dermal fillers, such as hyaluronic acid, are injected in the dermal layer to smooth out wrinkles and improve contours, but such fillers do not tighten or reduce laxity of the skin.

As such, a need exists for more effective treatments of these conditions that overcome the deficiencies associated with known treatment options. Accordingly, it is an objective of various embodiments of the present invention to address these and other needs.

BRIEF SUMMARY

The present invention specifically addresses and alleviates the deficiencies in the art. More specifically, there are disclosed topically-applied compositions and methods for treating loose skin and subcutaneous deposits of fat that contain one or more bleomycin-type compounds, that are present in an amount effective to cause apoptosis in targeted fat cells and tighten surrounding loose skin and connective tissue via displacement of such loose skin with fibrous tissue. In this regard, the compositions and methods of the present invention seek to utilize the well-known and understood properties of bleomycin to damage intracellular DNA that consequently leads to genomic instability in damaged cells. By selectively targeting localized areas of loose skin and subcutaneous fatty tissue via the administration of a topical composition that can be deployed upon discreet and selectively chosen areas of an individual's skin, the methods and composition of the present invention advantageously can produce a selectively chosen, localized effect upon any portion of the body where it is desired to displace loose skin and eliminate subcutaneous fatty tissue.

According to a preferred embodiment, the bleomycin is topically applied in a concentration ranging from 20 to 100,000 mgs per square decimeter of surface area of skin to be treated. In a more highly refined embodiment, the bleomycin is administered in an amount from 200 to 10,000 mgs per square decimeter of skin treated, and in a most highly preferred embodiment, it is administered in an amount ranging from 200 to 2,000 mgs per decimeter of skin to be treated.

With respect to the formulation of the compositions of the present invention, it is contemplated that the bleomycin will be mixed with other suitable carriers and/or excipients and formulated per conventional pharmaceutical manufacturing practices, including conventional mixing, dissolving, granulating, emulsifying, encapsulating, entrapping, or compression techniques that are readily known and understood in the art. The bleomycin component will be present in the composition in an amount ranging from 0.02 to 100 percent by weight; however according to a preferred embodiment, the bleomycin will be present in an amount from 0.2 to 10 percent by weight, and in a more highly preferred embodiment 0.2 to 2 percent by weight. The composition will also preferably be formed as a cream, lotion, ointment, gel, foam, wax, spray or other formulation for ease of topical application. The compositions may also be deployed via a transdermal patch.

With respect to the administration of such composition, the same will be topically applied directly upon the area of skin to be treated. To that end, it is contemplated that the compositions of the present invention may be applied as a one-time application or applied one to several times per day or over a series of days to the extent necessary to cause apoptosis in the fat cells and/or skin cells upon which the compositions are applied.

In an alternative embodiment, the bleomycin is formulated as an injectable composition wherein the bleomycin is injected in a concentration ranging from 2 to 10,000 mgs per square decimeter of surface area of skin to be treated. In a more highly refined embodiment, the bleomycin is injected in an amount from 20 to 1,000 mgs per square decimeter of skin treated, and in a most highly preferred embodiment, bleomycin is administered in an amount ranging from 20 to 200 mgs per decimeter of skin to be treated. As per the topical bleomycin formulations, the injectable bleomycin will be mixed with other suitable carriers and/or excipients and formulated per conventional pharmaceutical manufacturing practices. To that end, it is contemplated that other pharmaceutical compositions operative to impart a desired physiological and/or therapeutic effect may be included as part of such injectable formulation, which can include anti-inflammatories (i.e., injectable steroids), antibiotics, dispersion agents (i.e., detergents and/or hylauronic acid), adipolytic agents (i.e., deoxycholic acid) botulinum toxin, injectable fillers (i.e., hyaluronic acid, collagen), anesthetics (i.e., lidocaine, bupivacaine) and the like.

By virtue of the apoptosis induced by the bleomycin administered to the fat cells, coupled with the fact that the fat cells that are killed off will not grow back, it is believed the subsequent fat loss will be selective and permanent in nature. Moreover, with respect to loose skin, it is contemplated that the apoptosis mode of action caused by bleomycin will ultimately cause fibrous tissue to replace the loose skin per natural scarring and healing processes. As a consequence, the loose skin and underlying fatty deposits are essentially displaced with the fat cells dying off, never to return, and the loose skin ultimately being displaced with overexpressed collagen produced per the biological process of wound repair which, from a cosmetic perspective, is believed to be far more preferential than loose skin. Moreover, such approach is believed to be far superior than prior art treatment options currently available to try to address loose skin.

As such, loose skin and subcutaneous fat are eradicated in a substantially more effective and permanent manner than conventional invasive and non-invasive techniques. Moreover, because the active ingredient bleomycin is well-known in the art, it is understood that the compositions and formulations thereof may be readily practiced using known materials, formulations and manufacturing techniques readily understood in the art.

ments and that they are also intended to be encompassed within the scope of the invention.

The present invention is directed to compositions and methods for treating loose skin and deposits of subcutaneous fat that incorporate the use of one or more bleomycin-type drugs that are formulated to be topically applied to the areas of loose skin and fatty tissue sought to be treated. With respect to the active ingredient, bleomycin, the same is readily understood in the art and has been the subject of extensive testing and clinical usage. Exemplary of the numerous references associated with bleomycin include the following articles: Dorr, R T, *Bleomycin pharmacology: mechanism of action and resistance, and clinical pharmacokinetics*, Semin. Oncol., 1992, Apr. 19 (2Suppl 5) 3-8; Chen, et al., *Bleomycins: Towards better therapeutics*, Nature Reviews, February 2005, Vol 5, 102-112; Froudarakis, et al., *Revisiting bleomycin from pathophysiology to safe clinical use*, Critical Reviews in Oncology/Hematology, 87 (2013) 90-100, the teachings of all of which are expressly incorporated herein by reference.

In this regard, bleomycins are a group of anti-tumor antibiotics initially isolated from broths of *Streptomyces verticillus*. The most common versions of the drug are identified as A2, A5 and B2 and are the primary forms used clinically against cancer. For each form, the mode of action is well-understood and is directed to the ability of bleomycin to bind with DNA and subsequently cause breaks in the DNA sequence, which subsequently leads to cell death. Of the different types of bleomycin, approximately 60-70 percent of the type used clinically is bleomycin A2, the structure of which is reproduced herebelow:

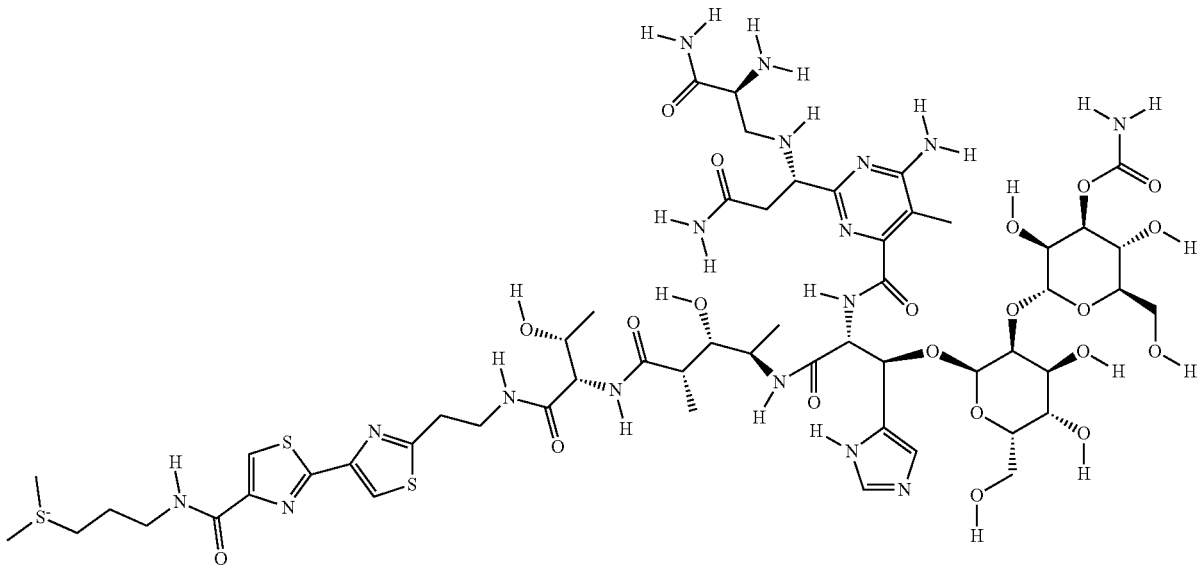 [SMILES: Cc1c(N)nc([C@H](CC(N)=O)NC[C@H](N)C(N)=O)nc1C(=O)N[C@@H](C(=O)N[C@H](C)[C@@H](O)[C@H](C)C(=O)N[C@H](C(=O)NCCc1nc(-c2nc(C(=O)NCCC[S-](C)C)cs2)cs1)[C@@H](C)O)[C@@H](O[C@@H]1O[C@@H](CO)[C@@H](O)[C@H](O)[C@@H]1O[C@H]1O[C@H](CO)[C@@H](O)[C@H](OC(N)=O)[C@@H]1O)c1cnc[nH]1]

DETAILED DESCRIPTION

The detailed description set forth below is intended as a description of the presently preferred embodiment of the invention, and is not intended to represent the only form in which the present invention may be implemented or performed. The description sets forth the functions and sequences of steps for practicing the invention. It is to be understood, however, that the same or equivalent functions and sequences may be accomplished by different embodi- Approximately 20-30 percent of the remainder of clinical product is in the form of bleomycin B2 with other analogs comprising about 5 percent of the total bleomycin usage.

Also included within such bleomycin family of related compounds is pingyangmycin, also known as bleomycin A5, which is produced by a variety of *Streptomyces verticillus, pingyangesis* m. sp., which is also an anti-tumor glycopeptide antibiotic that is extensively utilized in China as a substitution for bleomycin A2. The chemical structure for pingyangmycin is reproduced herebelow:

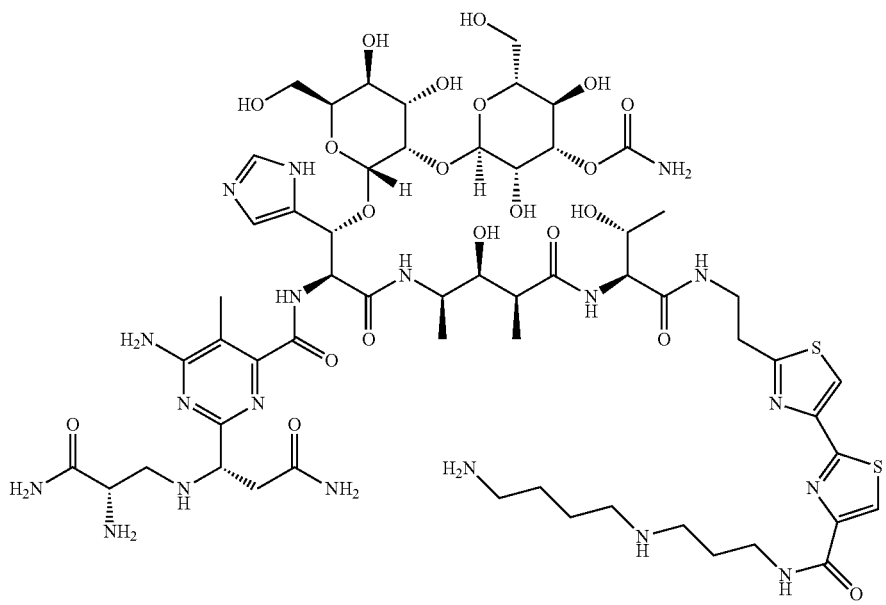 [SMILES: Cc1c(N)nc([C@H](CC(N)=O)NC[C@H](N)C(N)=O)nc1C(=O)N[C@H](C(=O)N[C@H](C)[C@@H](O)[C@H](C)C(=O)N[C@H](C(=O)NCCc1nc(-c2nc(C(=O)NCCCNCCCCN)cs2)cs1)[C@@H](C)O)[C@@H](O[C@@H]1O[C@@H](CO)[C@@H](O)[C@H](O)[C@@H]1O[C@H]1O[C@H](CO)[C@@H](O)[C@H](OC(N)=O)[C@@H]1O)c1cnc[nH]1]

For purposes of the present invention, pingyangmycin should be included as falling within the definition of a bleomycin-type drug as such composition, per the other potent bleomycin-type drugs of the present invention, are operative to bind with DNA, cause breakages in DNA and subsequently produce apoptosis.

With respect to the use of the bleomycin compounds to effectuate the treatment of loose skin and subcutaneous fatty tissue per the present invention, it is contemplated that a therapeutically effective amount of bleomycin constitutes a range from approximately 20 mg to 100000 mg of bleomycin per square decimeter of loose skin/fatty tissue to be treated. In further refinements of the invention, it is contemplated that a more optimal administration would comprise approximately 200 mg to 10000 mg of bleomycin per square decimeter of skin, and in a most highly preferred embodiment, a dosage of 200 mgs to 2000 mgs of bleomycin per square decimeter of skin.

With respect to the composition through which the bleomycin is topically administered, the same may take the form of a topically applied cream, lotion, ointment, gel, foam, wax, spray or any other formulation through which a medicament may be topically applied that contains from 0.02 to 100 percent by weight of bleomycin. In a preferred embodiment, the bleomycin will be present in an amount ranging from 0.2 to 10 percent by weight, and in a most highly preferred embodiment, will be present in an amount from 0.2 to 2 percent by weight. Such compositions may be applied as a single topical administration over the area of skin to be treated, or may be applied once to several times a day for a duration of several days so as to achieve the desired effect. To that end, it is contemplated that the compositions may be applied in a range ranging from 1 to 3 times per day from 1 to 180 days.

Advantageously, the compositions of the present invention will be formulated so as to be applied directly onto the skin by manual application or via a simple device, such as a roller or spray. Alternatively, to the extent desired, the compositions may be deployed through a conventional transdermal drug delivery system, such as a transdermal patch using transdermal delivery mechanisms well-known in the art. In this regard, the compositions of the present invention, as well as the manner by which the same are applied, are specifically formulated for localized application on discrete areas of the body where loose skin and/or deposits of subcutaneous fat are sought to be treated, and are specifically formulated and intended to be applied in a manner that does not involve any systemic distribution of the active bleomycin agents. Rather, the objectives of the present invention are to provide a composition and a manner of using the same that are exceedingly simple to administer and provide exceptionally effective treatment of loose skin and subcutaneous fat removal on only those portions of the body as selectively chosen by the individual user.

With respect to the formulation of compositions including bleomycin that may be administered topically and in effective amounts to achieve the treatment objectives discussed herein, it is understood that any of a variety of formulations and techniques known in the art may be utilized to derive such compositions. Exemplary of such compositions include those disclosed in Epstein, et al. *Topical Bleomycin for the Treatment of Dysplastic Oral Leukoplakia*, Cancer 1998; 83: 629-634; and K. G. Lau, et al., *Ultra-deformable liposomes containing bleomycin: In vitro stability and toxicity n human cutaneous keratinocyte cell lines*, International Journal of Pharmaceutics 300 (2005) 4-12, the teachings of which are expressly incorporated herein by reference. Additionally exemplary of compositions that may be formulated to contain effective amounts of bleomycin for topical application include those disclosed in U.S. Pat. No. 5,326,790 A, entitled ADMINISTRATION OF SKIN MEDICATIONS BY USE OF DICARBOXYLIC ACIDS AND DERIVATIVES, issued to Thornfeldt on Jul. 5, 1994; Published United States Patent Application Serial No. US2004/ 40224012 A1, entitled TOPICAL APPLICATION AND METHODS FOR ADMINISTRATION OF ACTIVE AGENTS USING LIPOSOME MACRO-BEADS, published Nov. 11, 2004 and filed in the name of Suvanprakorn et al.; and Published United States Patent Application No. US2014/0141100 A1, entitled COMPOUNDS AND METHODS FOR APPETITE SUPPRESSION AND WEIGHT CONTROL, published May 22, 2014 and filed in the name of Marino, et al., the teachings of all of which are expressly incorporated herein by reference. To that end, it is contemplated that the development and application of formulations such as bleomycin-nanoparticle or liposome-type or mineral complexes, as are well-known in the art, could be readily devised and implemented.

In all of such formulations, bleomycin is the active ingredient and combined with other ingredients for use in topical application. Furthermore, it will be appreciated by those skilled in the art that in addition to formulating such compositions for topical applications, other methodologies and/or compounds may be used to enhance the absorption of bleomycin so as to cause the bleomycin component to penetrate into the loose skin and underlying fatty deposits in order to produce the desired apoptosis effect on such target areas. For example, such bleomycin-containing pharmaceutical compositions may deploy additional components which act as an absorption promoter to facilitate the transport of the bleomycin in sufficient amounts into the skin in order to achieve the desired effect in the target area. Among the variety of techniques to improve drug skin penetration comprise pre-treating the targeted treatment site with a known method of physically penetrating the skin surface, with devices and methods like laser, electroporation, photodynamic therapy (PDT), dermabrasion and/or micro-needling. Other known techniques include chemical enhancers, physical enhancers, and formulation optimization, all of which are known and understood in the art. Exemplary of the teachings associated with the topical administration of agents such as bleomycin and how to optimize delivery the same include the teachings of Taveira et al., *Topical administration of anticancer drugs for skin cancer treatment*, C. La Porta, Ed/, pp. 247-272, 2011 and Dianzani, et al., *Drug delivery nanoparticles in skin cancer*, BioMed Research International, Vol. 2014 (2014), Article ID 895986, the teachings of both of which are expressly incorporated herein by reference.

Accordingly, it will be readily understood by those skilled in the art that such compositions are operative to be topically applied and become therapeutically effective insofar as the bleomycin will effectuate apoptosis of underlying fat cells, as well as to promote displacement of loose skin and fatty tissue with fibrous scarring. To that end, and as discussed above, it is believed that compositions for topical application that contain from 0.2 to 10 percent by weight of bleomycin will constitute a more targeted, localized effect, and in a most highly preferred embodiment, the bleomycin will be present in an amount from 0.2 to 2 percent by weight.

In an alternative variation of the present invention, the bleomycin compositions disclosed herein may be formulated for injection such that a known quantity of bleomycin is injected about a given surface area of skin. As per the aforementioned topically-applied embodiments, the injectable formulations of bleomycin may be formulated using known pharmaceutical manufacturing techniques and can include suitable carriers and/or excipients readily known and understood in the art. Per such injectable compositions, it is contemplated that according to a preferred embodiment the bleomycin will be injected in a concentration ranging from 2 to 10,000 mgs per square decimeter of surface area of skin to be treated. In a more highly refined embodiment, the bleomycin is injected in an amount from 20 to 1,000 mgs per square decimeter of skin treated, and in a most highly preferred embodiment, the bleomycin is administered in an amount ranging from 20 to 200 mgs per decimeter of skin to be treated. As discussed above, such injectable formulation may be made according to known manufacturing techniques and include known other agents that may be operative to impart a desired therapeutic and/or physiological effect. Along those lines, it is contemplated that excipients can include anti-inflammatories (i.e., injectable steroids), antibiotics, dispersion agents (i.e., detergents and/or hylauronic acid), adipolytic agents (i.e., deoxycholic acid) botulinum toxin, injectable fillers (i.e., hyaluronic acid, collagen), anesthetics (i.e., lidocaine, bupivacaine) and other agents known in the art. As discussed above, it is contemplated that such bleomycin formulations, although administered as part of a subcutaneous injection, will be operative to provide only a localized effect in the desired target area of skin. Such injections may also be administered as a single injection or multiple injections and given as a one-time therapy or over multiple days or months.

Advantageously, by virtue of the apoptosis mode of action, particularly with respect to fat cells, it is believed that the treatment will produce a permanent result insofar as fat cells do not regenerate and the fibrous tissue will permanently displace loose skin. Along those lines, it is believed that when utilizing such composition in the manner discussed above, the therapeutic and cosmetic results will be easily and readily attained and that the side effect profile will be consistent with that known in the literature with respect to bleomycin usage. As will be understood by those skilled in the art, conventional safety warnings and precautions to prevent adverse side effects and overuse of such compositions will be necessarily taken into consideration as based upon the well-known and extensively studied pharmacology associated with the use of bleomycin. Notwithstanding, it is believed that the compositions of the present invention and the use thereof provide an exceptionally safe and advantageously non-invasive methodology for eradicating loose skin and subcutaneous fate deposits in a manner that is exceptionally far more effective than conventional prior art methods.

Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention.

What is claimed is:

1. A method for displacing skin with fibrous connective tissue comprising the step of topically applying a composition containing an effective amount of at least one bleomycin-family drug upon the skin sought to be displaced.

2. The method of claim 1 wherein at least one bleomycin-family drug is selected from the group consisting of bleomycin A2, bleomycin A5, bleomycin B2 and pingyangmycin.

3. The method of claim 1 wherein said bleomycin-family drug is present in said composition in an amount ranging from 0.02 percent to 100 percent by weight.

4. The method of claim 1 wherein said bleomycin-family drug is administered in an amount upon said skin ranging from 20 mg to 10,000 mg per square decimeter of skin.

5. The method of claim 4 wherein said bleomycin-family drug is administered in an amount upon said skin ranging from 200 mg to 10,000 mg per square decimeter of skin.

6. The method of claim 5 wherein said bleomycin-family drug is administered in an amount upon said skin ranging from 200 mg to 2,000 mg per square decimeter of skin.

7. A method for removing subcutaneous fat comprising topically applying a composition containing an effective amount of at least one bleomycin-family drug upon said skin overlying said subcutaneous fat, said effective amount of said at least one bleomycin-family drug being operative to induce apoptosis within a majority of the fat cells making up said subcutaneous fat.

8. The method of claim 7 wherein at least one bleomycin-family drug is selected from the group consisting of bleomycin A2, bleomycin A5, bleomycin B2 and pingyangmycin.

9. The method of claim 7 wherein said composition is topically applied in a single application.

10. The method of claim 7 wherein said composition is applied from 1 to 3 times per day from 1 to 180 days.

11. The method of claim 7 wherein said composition is formulated to be applied as a composition selected from the group consisting of a cream, lotion, ointment, gel, foam, wax, and spray.

12. The method of claim 7 wherein said composition is formulated to be applied as a transdermal patch.

13. A method for displacing skin with fibrous connective tissue and removing subcutaneous fat disposed below said skin comprising the step of injecting a composition containing an effective amount of at least one bleomycin-type drug within the skin sought to be displaced, said bleomycin-family drug being selected from the group consisting of bleomycin A2, bleomycin A5, bleomycin B2 and pingyangmycin, said bleomycin-family drug being injected in a concentration ranging from 2 to 10,000 mgs per decimeter of surface area of skin to be treated.

14. The method of claim 13 wherein said bleomycin-family drug is injected in an amount from 20 to 1,000 mgs per square decimeter of skin to be treated.

15. The method of claim 13 wherein said bleomycin-family drug is injected in an amount from 20 to 200 mgs per square decimeter of skin to be treated.

* * * * *